US010525270B2

(12) United States Patent
Sheldon et al.

(10) Patent No.: US 10,525,270 B2
(45) Date of Patent: *Jan. 7, 2020

(54) METHODS FOR SETTING CARDIAC PACING PARAMETERS IN RELATIVELY HIGH EFFICIENCY PACING SYSTEMS

(71) Applicant: Medtronic, Inc., Minneapolis, MN (US)

(72) Inventors: Todd J Sheldon, North Oaks, MN (US); Wade M Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 804 days.

This patent is subject to a terminal disclaimer.

(21) Appl. No.: 14/605,040

(22) Filed: Jan. 26, 2015

(65) Prior Publication Data

US 2015/0190644 A1 Jul. 9, 2015
US 2016/0158557 A9 Jun. 9, 2016

Related U.S. Application Data

(63) Continuation of application No. 14/149,277, filed on Jan. 7, 2014, now Pat. No. 8,942,806, which is a
(Continued)

(51) Int. Cl.
*A61N 1/37* (2006.01)
*A61N 1/375* (2006.01)
*A61N 1/372* (2006.01)

(52) U.S. Cl.
CPC ......... *A61N 1/3712* (2013.01); *A61N 1/3708* (2013.01); *A61N 1/3756* (2013.01); *A61N 1/37205* (2013.01)

(58) Field of Classification Search
CPC ............... A61N 1/3708; A61N 1/3712; A61N 1/37205; A61N 1/3756
See application file for complete search history.

(56) References Cited

U.S. PATENT DOCUMENTS 5,320,643 A 6/1994 Roline et al.
5,350,401 A 9/1994 Levine
(Continued)

FOREIGN PATENT DOCUMENTS

CN 102028459 A 4/2011
EP 1 291 038 A2 3/2003
(Continued)

OTHER PUBLICATIONS (PCT/US2012/048123) PCT Notification of Transmittal of the International Search Report and the Written Opinion of the International Searching Authority.
(Continued)

*Primary Examiner* — Rex R Holmes (57) ABSTRACT

According to some methods, for example, preprogrammed in a microprocessor element of an implantable cardiac pacing system, at least one of a number of periodic pacing threshold searches includes steps to reduce an evoked response amplitude threshold for evoked response signal detection. The reduction may be to a minimum value measurable above zero, for example, as determined by establishing a 'noise floor'. Alternately, amplitudes of test pacing pulses and corresponding post pulse signals are collected and reviewed to search for a break, to determine a lower value to which the evoked response threshold may be adjusted without detecting noise. Subsequent to reducing the threshold, if no evoked response signal is detected for a test pulse applied at or above a predetermined maximum desirable pulse energy, an operational pacing pulse energy is set
(Continued)

to greater than or equal to the maximum desirable in conjunction with a reduction in pacing rate.

20 Claims, 5 Drawing Sheets

Related U.S. Application Data continuation of application No. 13/193,783, filed on Jul. 29, 2011, now Pat. No. 8,626,294.

(56) References Cited

U.S. PATENT DOCUMENTS

| | | | |
|---|---|---|---|
| 5,447,525 A | | 9/1995 | Powell et al. |
| 5,480,414 A | * | 1/1996 | Stroebel et al. ............... 607/28 |
| 5,873,898 A | | 2/1999 | Hemming et al. |
| 6,134,473 A | | 10/2000 | Hemming et al. |
| 6,144,881 A | | 11/2000 | Hemming et al. |
| 7,738,959 B2 | | 6/2010 | Manrodt et al. |
| 2003/0208241 A1 | * | 11/2003 | Bradley et al. ............... 607/27 |
| 2004/0064162 A1 | | 4/2004 | Manrodt et al. |
| 2004/0116973 A1 | * | 6/2004 | Ohman ............................ 607/27 |
| 2004/0172082 A1 | * | 9/2004 | Ferek-Petric .................. 607/27 |
| 2006/0212081 A1 | | 9/2006 | Suga et al. |
| 2007/0088397 A1 | | 4/2007 | Jacobson |

FOREIGN PATENT DOCUMENTS

| | | | | |
|---|---|---|---|---|
| EP | | 1 302 217 A2 | 4/2003 | |
| WO | | WO-2007047681 A2 * | 4/2007 | ............ A61N 1/056 |
| WO | | WO 2007047681 A2 | 4/2007 | |

OTHER PUBLICATIONS

Chinese first office action (English Language), application No. 201280037945.X, dated Dec. 22, 2014, 8 pages.

Chinese second office action (English Language), application No. 201280037945.X, dated Aug. 28, 2015, 9 pages.

Chinese first office action (Chinese Language), application No. 201280037945.X, dated Dec. 22, 2014, 8 pages.

Chinese second office action (Chinese Language), application No. 201280037945.X, dated Aug. 28, 2015, 10 pages.

* cited by examiner

METHODS FOR SETTING CARDIAC PACING PARAMETERS IN RELATIVELY HIGH EFFICIENCY PACING SYSTEMS

RELATED APPLICATION

This application is a continuation of U.S. patent application Ser. No. 14/149,277 filed Jan. 7, 2014 entitled "METHODS FOR SETTING CARDIAC PACING PARAMETERS IN RELATIVELY HIGH EFFICIENCY PACING SYSTEMS", issued Jan. 27, 2015 as U.S. Pat. No. 8,942,806, herein incorporated by reference in its entirety.

TECHNICAL FIELD

The present invention pertains to implantable cardiac pacing systems and more particularly to methods for setting pacing parameters in order to increase system efficiency.

BACKGROUND

Figure 1A:
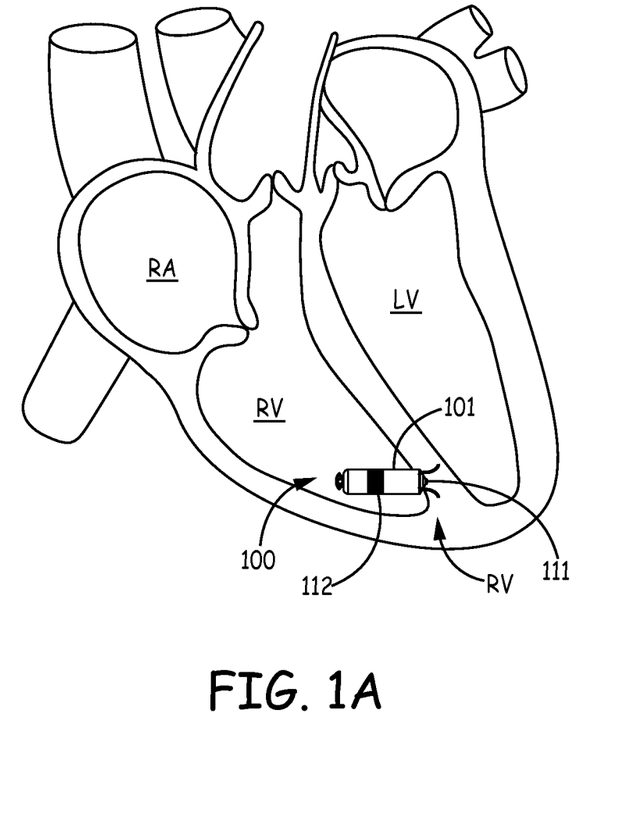
FIGS. 1A-B are schematics providing context for methods of the present invention.
Figure 1B:
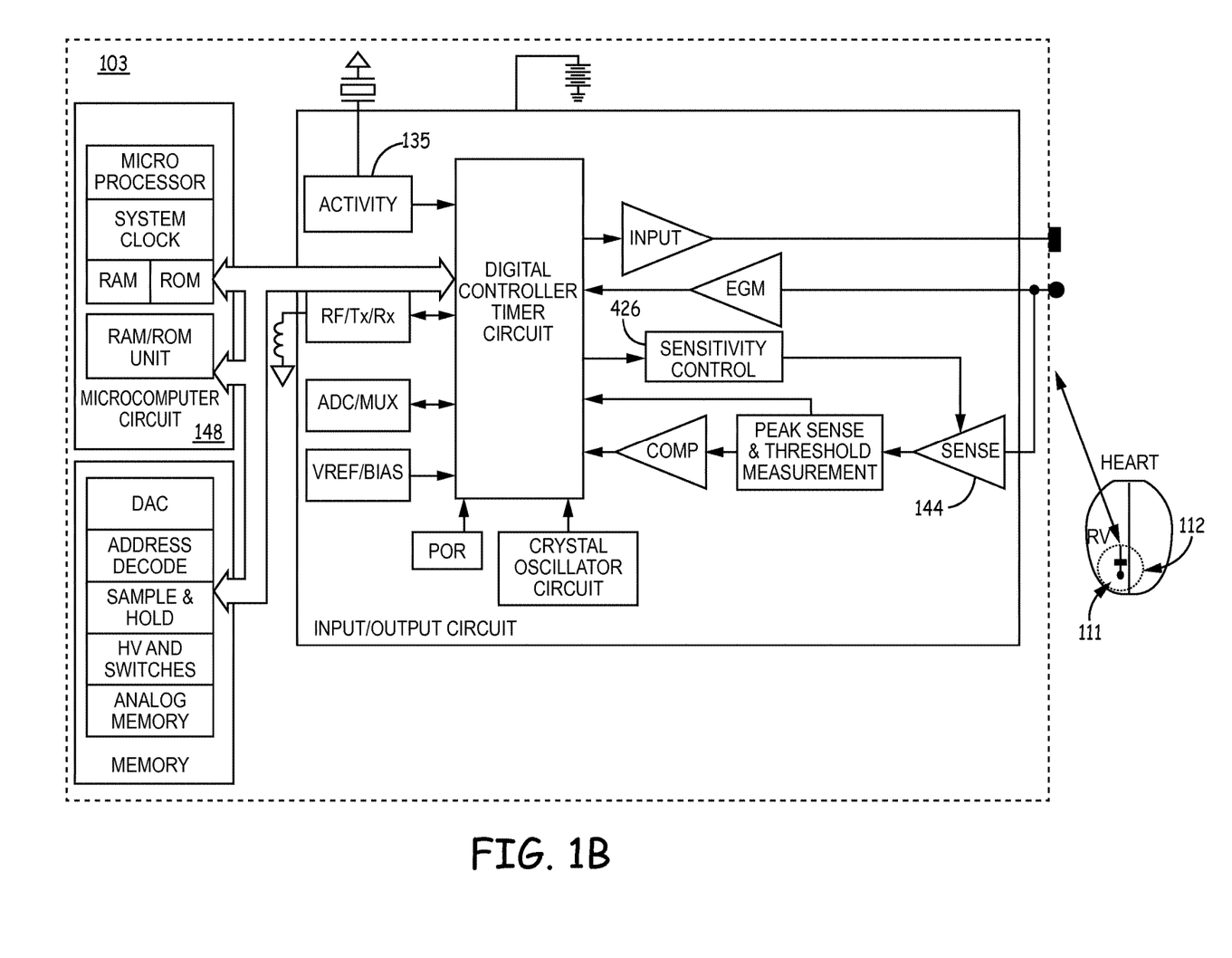

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications often associated with elongate lead wires, which are well known to those skilled in the art, have motivated the development of cardiac pacing systems that are wholly contained within a relatively compact package for implant in close proximity to the pacing site, for example, within the right ventricle RV of the heart. With reference to FIGS. 1A-B, such a system 100 is illustrated, wherein pace/sense electrodes 111, 112 are formed on an exterior surface of a capsule 101 that hermetically contains a pulse generator 103 (shown in FIG. 1B via a block diagram). FIG. 1A further illustrates tine members 115 mounted to an end of capsule 101, in proximity to electrode 111, in order to secure electrode 111 against the endocardial surface of RV, and electrode 112 offset distally from electrode 111. Capsule 101 is preferably formed from a biocompatible and biostable metal such as titanium overlaid with an insulative layer, for example, medical grade polyurethane or silicone, except where electrode 112 is formed as an exposed portion of capsule 101. An hermetic feedthrough assembly (not shown), such as any known to those skilled in the art, couples electrode 111 to pulse generator 103 contained within capsule 103.

With further reference to FIGS. 1A-B, those skilled in the art will appreciate that system 100, via electrodes 111, 112 and corresponding sense amplifier circuitry 144, has the capability to sense intrinsic ventricular depolarization (i.e. R-waves) and, in the absence of the intrinsic depolarization, to apply stimulation pulses to the RV in order to create paced ventricular depolarization. The amount of energy in each stimulation pulse, or the pulse energy is preferably set at the minimum value necessary to create the paced ventricular depolarization, that is, to capture the heart. A measure of the response of the heart muscle to the stimulation pulse, or the evoked response assures that this pulse energy is sufficient. Those skilled in the art are aware that measuring the evoked response may be confounded by post stimulation pulse polarization, and a number of prior art disclosures are directed toward methods for dealing with this issue. Commonly assigned U.S. Pat. No. 6,144,881 (to Hemming et al.), which is hereby incorporated by reference, in its entirety, describes suitable methods and apparatus (i.e. capture detection circuitry) for reliably and accurately detecting an evoked response in a sensed signal that follows a pacing pulse, by rejecting, or filtering out post pulse polarization contributions to the sensed signal, when the evoked response contribution to the sensed signal meets a minimum amplitude criterion.

Utilizing the apparatus and methods taught by the '881 reference to conduct periodic pacing threshold searches can assure, in most cases, that pacing pulse energies are not greater than necessary to capture the heart. But, particularly in the context of recently developed relatively compact pacing systems, like that shown in FIG. 1A, there is a desire to take additional steps toward even greater system efficiency.

SUMMARY

According to some methods of the present invention, which may be preprogrammed in a microprocessor element of an implantable cardiac pacing system of the present invention, at least one of a number of periodic pacing threshold searches includes a step to adjust an initial evoked response amplitude threshold for evoked response signal detection to a lower value when, upon applying a test pacing pulse, no evoked response signal is detected at the initial evoked response threshold. During such a pacing threshold search, according to some methods, adjustment of the evoked response threshold is triggered by an applied test pacing pulse that has an energy level above a predetermined maximum desirable pulse energy, when no corresponding evoked response signal is detected at the initial evoked response threshold. But, according to alternate methods, no such condition is necessary to trigger steps toward reducing the initial evoked response threshold. Subsequent to reducing the evoked response threshold, if no evoked response signal is detected at the lower evoked response threshold, when another test pulse is applied at the predetermined maximum desirable pulse energy, preferred methods determine and set an appropriate operational pacing pulse energy, which is either greater than or equal to the predetermined maximum desirable pulse energy, and, in concert, reduce a pacing rate.

During a pacing threshold search, an evoked response threshold may be adjusted by a predetermined decrement, or adjusted to a minimum amplitude measurable above zero, for example, as determined by establishing a 'noise floor' by applying test pacing pulses at minimum and maximum energy levels and reviewing corresponding post pulse signals, according to some methods. Alternately, or in addition, amplitudes of test pacing pulses and corresponding amplitudes of post pulse signals (a.k.a. potential evoked response signals) are collected (data collection), during a pacing threshold search, and then processed, or reviewed, to search for a break (significant difference) between post pulse signal amplitudes corresponding to different (i.e. adjacent) pacing pulse energies, in order to determine a lower value to which the evoked response threshold may be adjusted. According to some methods, the collection of such data and the processing thereof, to establish a lower evoked response threshold, are implemented in a dynamic fashion during incrementing and decrementing loops of a pacing threshold search.

Warning signals may be generated by the pacing system, according to some methods, in concert with any one or a number of actions including, but not limited to: reducing the pacing rate (when the operational pacing pulse energy is set greater than or equal to the maximum desirable, following attempts to reduce the evoked response threshold for evoked response signals); adjusting the evoked response threshold to a lower value; adjusting the evoked response threshold to a minimum value measurable above zero; adjusting the evoked response threshold to a lower value multiple times, in multiple pacing threshold searches, in one day.

BRIEF DESCRIPTION OF THE DRAWINGS

The following drawings are illustrative of particular embodiments and methods of the present invention and therefore do not limit the scope of the invention. The drawings are not to scale and are intended for use in conjunction with the explanations in the following detailed description. Methods of the present invention will hereinafter be described in conjunction with the appended drawings wherein like numerals denote like elements.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Although FIGS. 1A-B provide context for the subsequent description, those skilled in the art will appreciate that alternative configurations of implantable pacing systems can employ the methods disclosed herein.

As described above, FIG. 1A illustrates pacing system 100 wholly implanted against an endocardial surface within the right ventricle RV, wherein electrodes 111, 112 are configured to sense electrical activity of the heart and apply pacing stimulation, when necessary, to adequately support the patient, as controlled by pulse generator 103, which is hermetically contained within capsule 101 and shown via block diagram in FIG. 1B. FIG. 1B illustrates the electronic components of pulse generator 103 including a microcomputer circuit 148, known to those skilled in the art, wherein a microprocessor element thereof may be preprogrammed to direct pulse generator 103 to execute any of the methods of the present invention. Although not shown, an appropriate implantable battery power source is preferably included within capsule 101 to power the electrical components of pulse generator 103. In order to facilitate evoked response detection, electrodes 111, 112 are preferably configured for the reduction of post stimulation polarization, according to methods known in the art, for example, with respect to maximized spacing therebetween and the microscopic morphology of the electrode surfaces.

Figure 2:
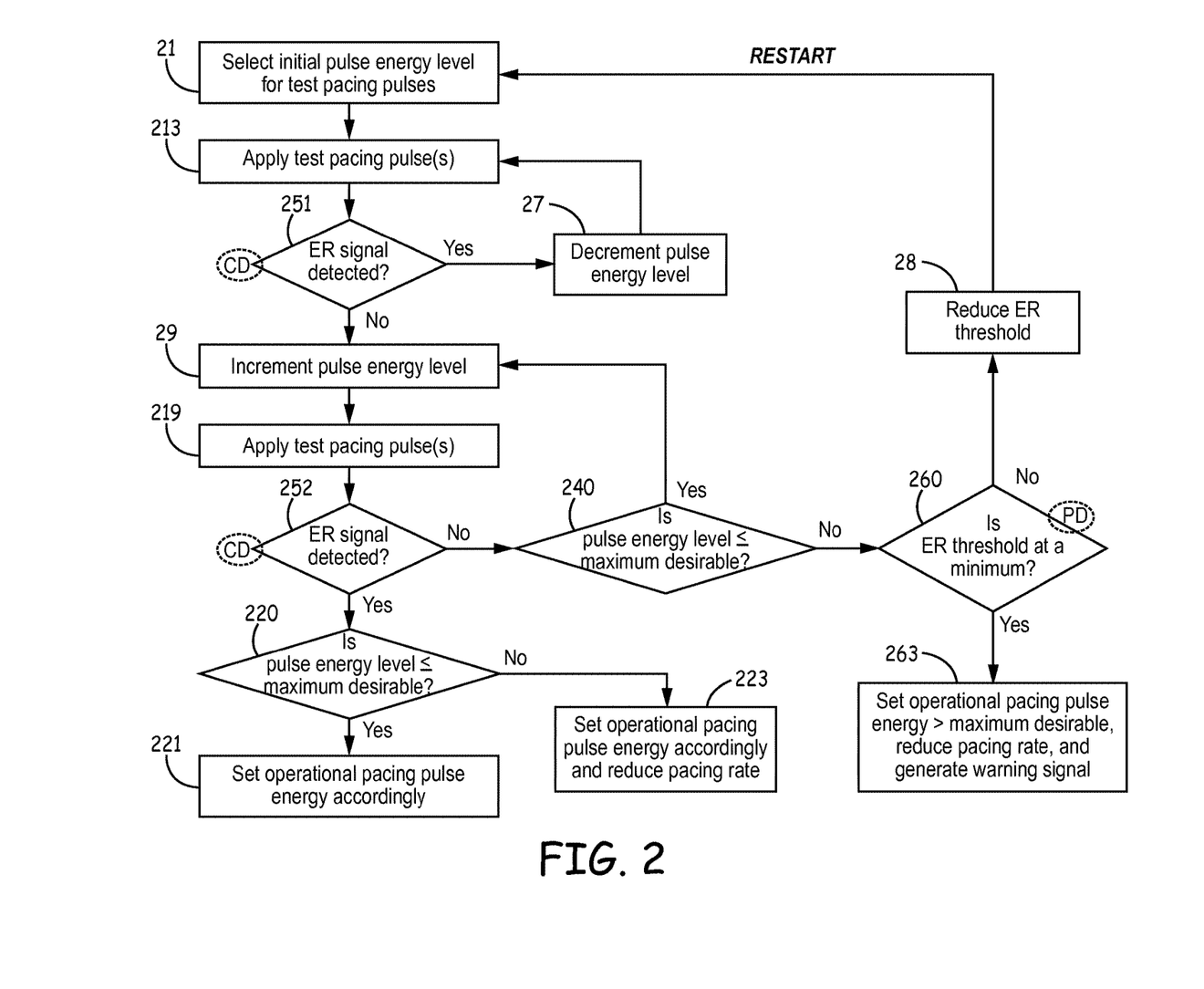
FIGS. 2, 2B, and 3 are flowcharts outlining some alternate methods of the present invention.
Figure 3:
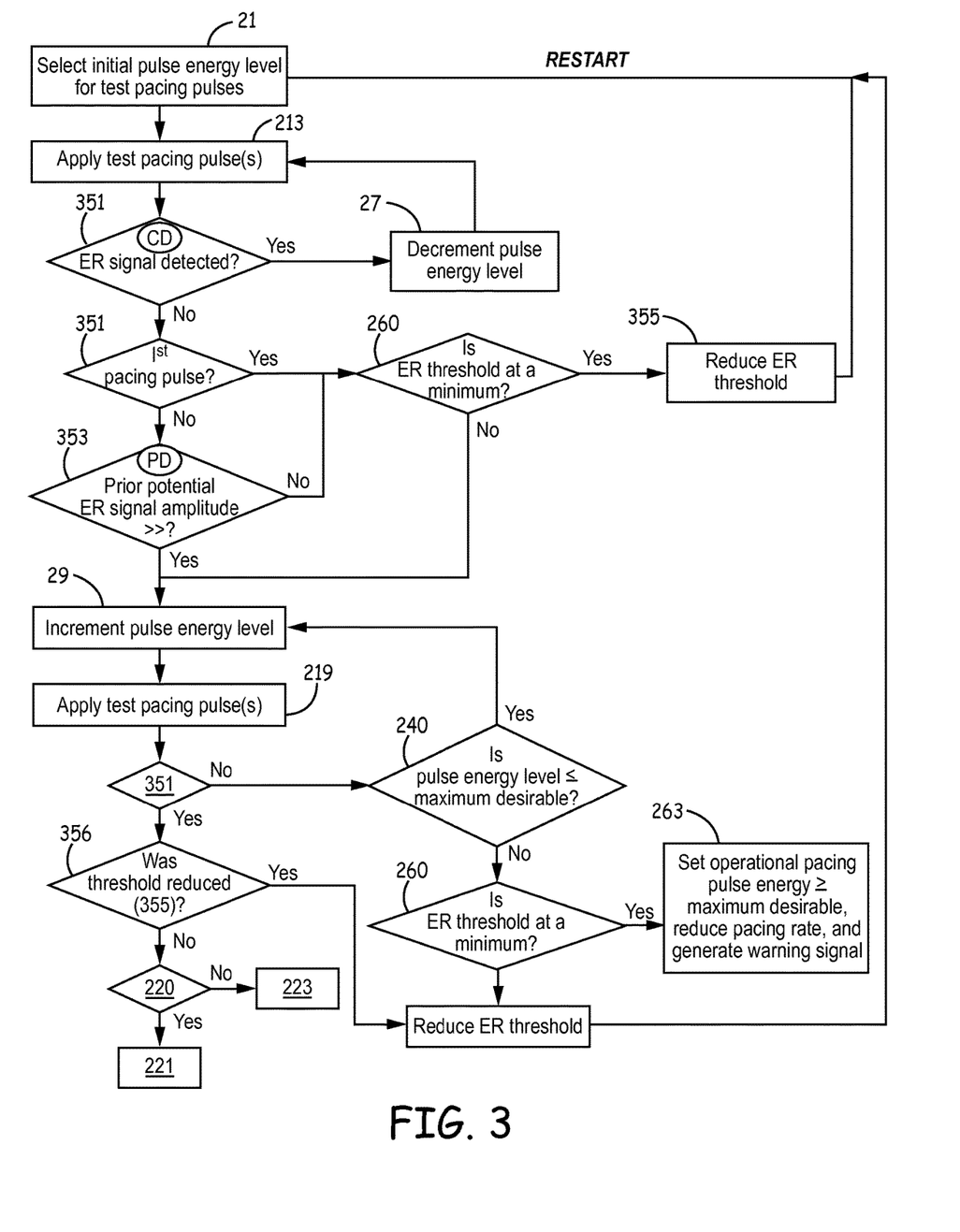

FIGS. 2 and 3 are a flowcharts outlining some alternative methods that are related to the detection of evoked response (ER) signals during a pacing threshold search, and which include steps to adjust an evoked response amplitude threshold for of ER signal detection during the pacing threshold search. The aforementioned and incorporated-by-reference U.S. Pat. No. 6,144,881, illustrates several exemplary waveforms from which ER signals may be detected, some corresponding to current flow through first order capture detection circuitry and others corresponding to second order negative peak detection circuitry, for example, in FIGS. 15(a)-15(c) and in FIGS. 16(a)-16(c), respectively, thereof. These types of detection circuitry, which are described in detail by the '881 incorporated-by-reference U.S. patent, or any other type of suitable circuitry, may be employed to carry out the methods disclosed herein.

The methods outlined by the flowcharts of FIGS. 2 and 3 may be incorporated within an overall capture management algorithm, which is employed by pulse generator 103 according to a preprogrammed schedule for conducting the periodic pacing threshold searches, and with conditions that must be met prior to conducting each search, for example, generally according to the description in column 12, lines 18-36 and FIG. 3 of commonly assigned U.S. Pat. No. 7,738,959, which passage and Figure are hereby incorporated by reference. Those skilled in the art appreciate the importance of these periodic pacing threshold searches to assure that pacing stimulation is effective (if capture is not continuously monitored), and to assure that the operational pacing pulse energy is not greater than that which is necessary to capture the heart with a given safety margin. In preferred embodiments, continuous capture monitoring assures adequate operational pacing pulse energy so that pacing threshold searches conducted according to the methods disclosed herein are directed more toward maintaining an operational pacing pulse energy at or below a maximum desirable energy level in order to increase system efficiency. It should be noted that what is designated herein as the maximum desirable energy level is a level, which is less than a maximum possible output, and which is predetermined based upon system operating characteristics to achieve the minimum acceptable operating efficiency, for example, to maintain an acceptable battery life for the system. For example, an amplitude of pacing pulses at the maximum desirable energy level is approximately 2.5 V, when an approximately 5 V pacing pulse amplitude is the maximum possible output.

With reference to FIGS. 2 and 3, an initial pulse energy level for the pacing threshold search, per step 21, is preferably set to a value that is less than the current operational pacing pulse energy, for a first application of one or more test pacing pulses, per step 213. If an ER signal is detected at decision point 251, then the pulse energy level is reduced, by a predetermined decrement, per step 27, for the application of subsequent pacing pulses back at step 213, otherwise the pulse energy level is increased, by a predetermined increment, per step 29, for the application of subsequent pacing pulses at step 219. Following step 219, if an ER signal is detected (decision point 252) and the pulse energy level is less than or equal to a maximum desirable energy level (decision point 220), the operational pacing pulse energy is set accordingly, per step 221. But, if an ER signal is not detected and the pulse energy level is less than or equal to the maximum desirable energy level (decision point 240), the energy level is again incremented, per step 29, for another application of test pacing pulses, per step 219. The above-described steps, which are designated by a surrounding dotted line in FIG. 2, generally correspond to a typical rheobase and chronaxie threshold test known in the art, for example, as described in greater detail by the aforementioned '959 Patent in column 12, line 39—column 13, line 2 and in column 13, lines 27-32, which passages are hereby incorporated by reference.

According to methods outlined by FIG. 2, when, at decision point 240, the pulse energy level is not less than or equal to the maximum desirable energy level, additional steps are taken to scrutinize an ER amplitude threshold for ER signal detection, in order to determine if this threshold can be reduced to find a lower pulse energy level effective to capture the heart. At decision point 260, which follows decision point 240, if the ER amplitude threshold is not already at a minimum, the ER threshold is reduced, per step 28, and then the pacing threshold search is restarted at step 21, and, if this search subsequently ends at step 221, then, in addition to setting the operational pacing energy, the lower/reduced amplitude ER threshold, per step 28, is preferably established as the initial ER threshold for a subsequent pacing threshold search. If, in one or more of the subsequent searches, similar steps are necessary to again reduce the ER threshold, a warning signal may be generated by the pulse generator, for example, an audible alarm which alerts the patient to contact his clinician.

Figure 2B:
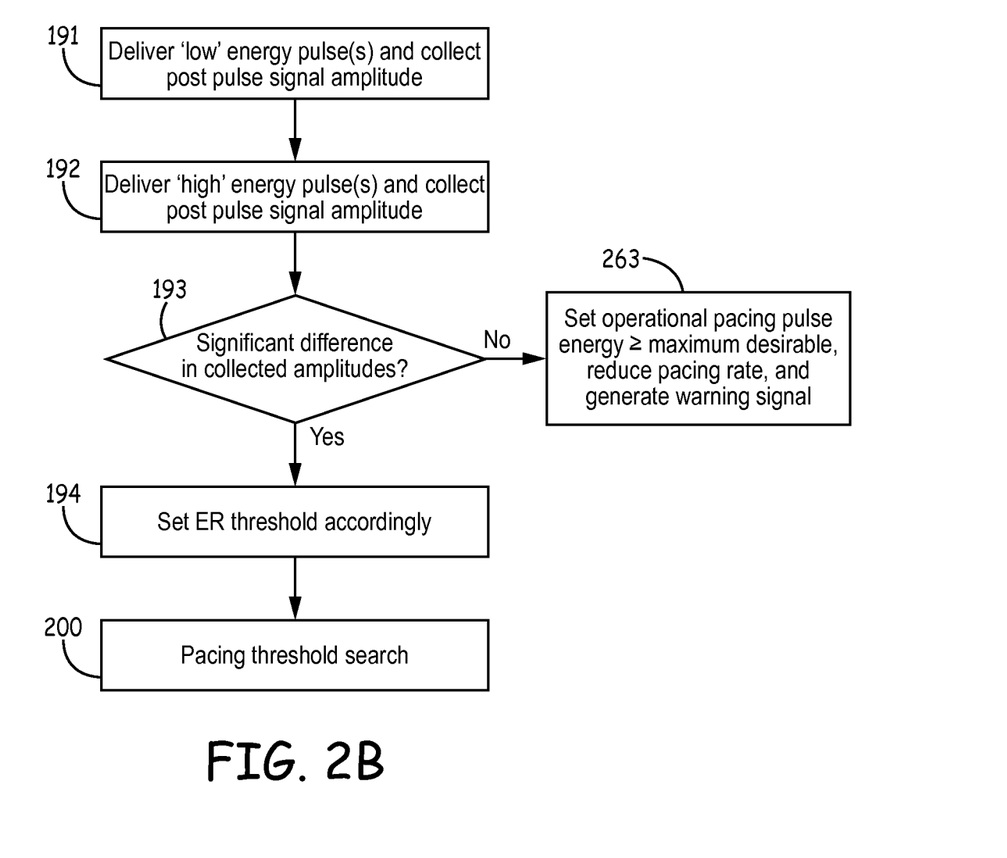

With further reference to FIG. 2, at step 28, the ER threshold may be immediately reduced to a minimum value, for example, a minimum measurable value just above zero, based upon general signal conditioning characteristics and noise patterns of the system, which may be determined at, or prior to, decision point 260, for example, by applying a pacing pulse of maximum pulse energy (i.e. highest output) followed by one of minimum pulse energy (i.e. at or just above zero) and collecting post pulse signal amplitudes for comparison. This determination may even take place preemptively, prior to step 21, according to the flow chart of FIG. 2B, wherein the typical pacing threshold test 200 is preceded by steps 191-194. If a significant difference is noted between the post pulse signal amplitudes, a 'noise floor' may be established according to the post pulse signal amplitude corresponding to the minimum energy pacing pulse, and the ER threshold set (step 194) either to a value just above the noise floor, for example, by a predetermined offset, or to a value midway between the noise floor and the initial ER threshold. Of course, if no significant difference between the post pulse signal amplitudes corresponding to the minimum and maximum pulse energy paces is found, the operational pacing pulse energy is set to an appropriate level, at or above the maximum desirable, in conjunction with a reduction in pacing rate and generation of a warning signal, per step 263. Step 263 will be described in greater detail below.

According to some alternate methods, the ER threshold may be reduced by a decrement that may not immediately set the threshold to a minimum value, wherein the decrement is determined by processing/reviewing data (designated by optional process data point PD at decision point 260), which was collected in prior steps, for example, as indicated by optional collect data points CD at decision points 251 and 252. For example, following each application of a test pacing pulse, at one or both of decision points 251 and 252, a voltage amplitude of the pacing pulse and an amplitude of the corresponding post pulse signal, hereinafter called a potential ER signal, are collected and stored for processing at decision point 260, in order to find, if possible, a lower ER amplitude threshold for ER signal detection, which is then implemented at step 28. The collected post pulse signals are designated herein as potential ER signals, since, even if the signal does not initially exceed the standing/current ER threshold, the signal may be an actual ER signal that is detectable once the ER threshold is reduced. Table 1, below, illustrates an example of how a collection of potential ER signal amplitudes and corresponding pacing pulse voltage amplitudes may be processed/reviewed, for example, at process data point PD, to find a break, or significant difference between potential ER signals of adjacent pacing pulse energies (i.e. ≥0.2 mV).

TABLE 1

| Pacing pulse amplitude (Volts) | Potential ER signal amplitude (millivolts) | |
|---|---|---|
| 3.5 | 0.5 | |
| 3 | 0.5 (initial threshold) | |
| 2.5 | 0.4 | |
| 2 | 0.4 | } break |
| 1.5 | 0.1 | |
| 1 | 0.1 | |

According to the illustrated example, a break is found between adjacent test pulse energy levels, as indicated by the bracket, so the ER threshold is reduced, at step 28, to a value that is greater than that on the low side of the break and less than or equal to the value on the high side of the break. Alternatively, if no break is found, the ER threshold may be reduced, per step 28, either according to a predetermined decrement or to the minimum measurable value above zero, as described above. It should be noted that, according to some alternate methods, an initial reduction of the ER threshold, per step 28, may be accomplished according to a predetermined decrement, and then the data collection and processing, like that illustrated in Table 1, may be employed in the subsequent search, restarted at step 21.

With further reference to decision point 260, if the ER threshold is already at a minimum, step 263 is taken to set the operational pacing pulse energy at an appropriate level, which is at or above the maximum desirable energy level, in conjunction with a reduction in pacing rate and generation of a warning signal to alert the patient to contact his clinician. According to some methods, step 263 includes a search for a pacing threshold above the maximum desirable (i.e. as outlined within the surrounding dotted line of FIG. 2, without the limitations of decision points 220 and 240), and, if found, sets the operational pacing pulse energy accordingly. But according to alternate methods, if a pacing threshold at or below the maximum desirable energy level cannot be found, after the steps are taken to search for a lower ER threshold, whether or not any pacing threshold is found in the range from maximum desirable to maximum possible, the operational pacing pulse energy is preferably set to the maximum desirable energy level, to avoid battery depletion before the patient can meet with his clinician. Note that the warning and/or reduced rate associated with step 263 may only be set if the pulse energy level is not found less than or equal to the maximum desirable multiple times in a row, according to some methods. For example, decision points 240 and 260 may lead to an abort and retry at a later time instead of step 263, and then after a second retry, step 263 is taken.

Turning now to FIG. 3, additional alternate methods are outlined wherein the above-described data collection and processing to establish a lower ER amplitude threshold for ER signal detection are implemented in a more dynamic fashion during incrementing and decrementing loops (above and below, respectively, the dashed line in FIG. 3) of a pacing threshold search. Thus, as will be seen from the ensuing description, the method outlined by FIG. 3 dictates a more aggressive approach to reducing the ER threshold than those outlined in FIG. 2, since scrutiny of the ER threshold, and subsequent reduction, is not necessarily dependent upon a pulse energy level being found greater than the maximum desirable energy level at decision point 240 of FIG. 2.

With reference to decision point 351 in FIG. 3, whether or not an ER signal is detected, a pacing pulse amplitude and a corresponding potential ER signal amplitude are collected, as indicated by the collect data point CD; and, once the pacing pulse energy is minimized, for example, via decrement step 27, to the point that no ER signal is detected, the collected data is processed at decision point 353, as designated by process data point PD. At decision point 353, if the prior collected potential ER signal amplitude (i.e. prior to the last one that did not meet the initial ER threshold) is not significantly greater (>>) than the last one, then the ER threshold is reduced, per step 355, and the pacing threshold search restarted at step 21 to determine if a lower pacing threshold can be found with the reduced ER threshold. Alternately, if the prior collected potential ER signal amplitude is significantly greater than the last, then the pacing pulse energy level is incremented, per step 29, for applied test pacing pulse(s), at step 219. Note that, if no ER signal is detected for the very first test pacing pulse of the threshold test, then the ER threshold is immediately reduced, as conditioned by decision point 352, and the pacing threshold test restarted. Of course, in either case, at decision point 260, if the ER threshold is already found to be at a minimum, the pacing pulse energy is incremented at step 29.

Following step 219, if no ER signal is detected, at another decision point 351, and the incremented pulse energy level is not found to be greater than the maximum desirable, at decision point 240, then the method loops back to step 29. If, at decision point 240, the pulse energy level is not found to be less than or equal to the maximum desirable, then the pending ER threshold is reviewed and, at decision point 260, if the ER threshold is not yet minimized, the threshold is reduced at step 357 and the pacing threshold search is restarted at step 21. Like the method outlined in FIG. 2, at decision point 260, if the ER threshold is found to already be minimized, step 263 is taken, according to any of the alternative methods described above.

If, at the decision point 351 that follows step 219, an ER signal is detected, then, if the ER threshold was previously reduced (step 355), as determined at decision point 356, then this threshold is again reduced, per step 357, and the pacing threshold search is restarted at step 21. Alternately, if the ER threshold was not previously reduced, then decision point 220 is encountered resulting in either step 221 or step 223, according to the above-described method outlined in FIG. 2. It should be noted that decision point 220 and steps 221 and 223 in the FIG. 3 flow chart are that same as those of the FIG. 2 flow chart and are designated only with the corresponding reference numeral.

If, after minimizing the ER amplitude threshold for ER signal detection as much as possible, by any of the above described method steps, the determined pacing threshold is still at an operational pulse energy level which is higher than the maximum desirable level, then, with reference to step 223 (FIGS. 2, 2B, and 3), the pacing rate is reduced, which, in addition to conserving energy at a higher pulse output, may induce symptoms to let the patient know that a follow-up visit with a clinician is necessary. In the instance that no ER signal is detected during the pacing threshold search, even when, as determined at decision point 260, the ER threshold is minimized to the lowest possible value, step 263 is taken. At step 263, a warning signal, such as the aforementioned audible alarm, is generated to alert the patient, and the operational pacing pulse energy level is preferably set to the maximum desirable (as opposed to a level that is in the range from the maximum desirable to the maximum possible), which, in conjunction with the reduced pacing rate, conserves battery energy until the patient meets with his clinician. Likewise, at step 223, rather than setting the operational pacing pulse energy level to one greater than the maximum desirable, as found in the pacing threshold search, the operational pacing pulse energy level is set to the maximum desirable in order to further preserve battery life. Some preferred methods also include a step of generating the warning signal, if, over the course of between two and three days, subsequent periodic pacing threshold searches end up with the reduced pacing rate of step 223. However, if in subsequent periodic pacing threshold searches within this time frame, an ER signal is detected for pacing pulses at an energy level that is less than or equal to the maximum desirable level, so that the operational pulse energy level can be reduced, the pacing rate will be increased back to an appropriate (i.e. non-symptomatic) rate.

The aforementioned preprogrammed schedule for conducting the periodic pacing threshold searches may dictate that pacing threshold searches be conducted at least once a day, yet increased in number, depending on outcome (i.e. greater than or equal maximum operational pacing pulse energy). Furthermore, a pacing threshold search that includes scrutiny of the ER threshold, for example, according to any of the above-described methods, may, preferably, only be triggered if a prior pacing threshold search results in the operational pacing pulse energy being set at the maximum desirable; and a limit may be placed on the number of this type of search conducted per day, for example, no more than three per day, according to some methods.

In the foregoing detailed description, the invention has been described with reference to specific embodiments. However, it may be appreciated that various modifications and changes can be made without departing from the scope of the invention as set forth in the appended claims.

We claim:

1. An implantable cardiac pacing system configured to be wholly implanted on or in a patient's heart, the system including a pulse generator having a microprocessor based control circuit, the control circuit comprising:
   means for triggering periodic pacing threshold searches, wherein the periodic pacing threshold searches comprise applying a series of test pacing pulses at incremented and/or decremented levels of pulse energy and detecting evoked responses thereto;
   means for setting an operational pacing pulse energy based upon the results of the pacing threshold search;
   means for reducing a pacing rate responsive to the operational pacing pulse energy being set greater than a predetermined maximum desirable pulse energy;
   means for defining an initial evoked response sensing threshold and responsive to no evoked response signal being detected at the initial evoked response sensing threshold following a test pacing pulse, adjusting the evoked response sensing threshold to a lower value; and
   means for triggering a pacing threshold search using the lower value for the evoked response amplitude threshold, responsive to the initial threshold being adjusted.

2. The system of claim 1, wherein the control circuit further comprises:
   means for generating a first command signal to set an operational pacing pulse energy greater than or equal to the predetermined maximum desirable pulse energy, responsive to no evoked response signal being detected with the lower evoked response amplitude threshold, following a test pacing pulse applied at or above a predetermined the maximum desirable pulse energy during the pacing threshold search.

3. The system of claim 2, wherein the applied test pacing pulse that triggers the adjusting of the initial evoked response amplitude threshold has an energy level above the predetermined maximum desirable pulse energy of the levels of pulse energy.

4. The system of claim 1, wherein the lower value for the evoked response amplitude threshold is a minimum value measurable above zero.

5. The system of claim 4, further comprising means for generating a warning signal in response to adjusting of the initial evoked response amplitude threshold to the lower value.

6. The system of claim 1, wherein the pacing threshold search further comprises:
collecting an amplitude of each test pacing pulse and corresponding potential evoked response signal, during the applied series of test pacing pulses;
wherein adjusting the initial evoked response amplitude threshold to the lower value comprises processing the collected amplitudes to search for a break between a first potential evoked response signal amplitude associated with a first test pacing pulse of the series and a second potential evoked response signal amplitude associated with a second test pacing pulse of the series, the first and second test pacing pulses having pacing energies adjacent one another; and
the lower value of the evoked response amplitude threshold is greater than a value of the lower of the first and second potential evoked response signal amplitudes and less than or equal to a value of the higher of the first and second potential evoked response signal amplitudes.

7. The system of claim 1, wherein restarting the pacing threshold search with the lower value for the evoked response amplitude threshold comprises:
collecting an amplitude of each test pacing pulse and corresponding potential detected evoked response signal, during the applied series of test pacing pulses;
processing the collected amplitudes to search for a break between a first potential evoked response amplitude associated with a first test pacing pulse of the series and a second potential evoked response signal amplitude associated with a second test pacing pulse of the series, the first and second test pacing pulses having pacing energies adjacent one another;
further adjusting the lower value of the evoked response amplitude threshold to an even lower value, responsive to the break being found, the even lower value being greater than a value of the evoked response amplitude of the lower of the first and second potential evoked response signal amplitudes; and
restarting the pacing threshold search with the even lower value of the evoked response amplitude threshold, responsive to the lower value being adjusted.

8. The system of claim 1, further comprising means for generating a warning signal in response to reducing the pacing rate.

9. The system of claim 1, wherein the control circuit further comprises means for conducting successive pacing threshold searches of the periodic pacing threshold searches with the lower value for the evoked response amplitude threshold, responsive to the reduction of the pacing rate; and
wherein the system further comprises means for generating a warning signal, responsive the pacing rate remaining reduced following each of at least two successive pacing threshold searches.

10. The system of claim 1, wherein the control circuit further comprises:
means for conducting a successive pacing threshold search of the periodic pacing threshold searches with the lower value for the evoked response amplitude threshold, responsive to the reduction of the pacing rate; and
means for setting the operational pacing pulse energy less than or equal to the maximum desirable pulse energy and for increasing the pacing rate responsive to an evoked response signal being detected at the lower threshold in the successive pacing threshold search.

11. The system of claim 10, wherein the control circuit conducts the at least one of the periodic pacing threshold searches, only if a prior pacing threshold search resulted in the operational pacing pulse energy being set at the predetermined maximum desirable pulse energy.

12. An implantable cardiac pacing system configured to be wholly implanted on or in a patient's heart, the system including a pulse generator having a microprocessor based control circuit, the control circuit comprising:
means for triggering periodic pacing threshold searches, wherein the periodic pacing threshold searches comprise applying a series of test pacing pulses at incremented and/or decremented levels of pulse energy and detecting evoked responses thereto;
means for setting an operational pacing pulse energy based upon the results of the pacing threshold search; and
means for reducing pacing rate responsive to the operational pacing pulse energy being set greater than a predetermined maximum desirable pulse energy; and
wherein the at least one of the periodic pacing threshold searches comprises no more than three per day.

13. The system of claim 1, wherein the system further comprises means for generating a warning signal responsive to the at least one of the periodic pacing threshold searches comprising more than one pacing threshold search in one day and the initial evoked response amplitude threshold in each of the searches being adjusted to the lower value.

14. The system of claim 12, further comprising means for generating a warning signal in response to reducing the pacing rate.

15. The system of claim 12 wherein the control circuit further comprises means for defining an initial evoked response sensing threshold and responsive to no evoked response signal being detected at the initial evoked response sensing threshold following a test pacing pulse, adjusting the evoked response sensing threshold to a lower value;
means for triggering a pacing threshold search using the lower value for the evoked response amplitude threshold, responsive to the initial threshold being adjusted; and
means for generating a first command signal to set an operational pacing pulse energy greater than or equal to the predetermined maximum desirable pulse energy, responsive to no evoked response signal being detected with the lower evoked response amplitude threshold, following a test pacing pulse applied at or above a predetermined the maximum desirable pulse energy during the pacing threshold search.

16. An implantable cardiac pacing system configured to be wholly implanted on or in a patient's heart, the system including a pulse generator having a microprocessor based control circuit, wherein the control circuit is configured to:

trigger periodic pacing threshold searches, wherein the periodic pacing threshold searches comprise the pulse generator applying a series of test pacing pulses at incremented and/or decremented levels of pulse energy and detecting evoked responses thereto;

set an operational pacing pulse energy for the pulse generator based upon the results of the pacing threshold search; and reduce a pacing rate of the pulse generator responsive to the operational pacing pulse energy being set greater than a predetermined maximum desirable pulse energy;

define an initial evoked response sensing threshold;

in response to no evoked response signal being detected by the pulse generator at the initial evoked response sensing threshold following a test pacing pulse, adjust the evoked response sensing threshold to a lower value; and trigger a pacing threshold search by the pulse generator using the lower value for the evoked response amplitude threshold, in response to the initial threshold being adjusted.

17. The system of claim 16, wherein the control circuit is further configured to:

generate a first command signal to the pulse generator to set an operational pacing pulse energy greater than or equal to the predetermined maximum desirable pulse energy, in response to no evoked response signal being detected with the lower evoked response amplitude threshold following a test pacing pulse applied at or above a predetermined the maximum desirable pulse energy during the pacing threshold search.

18. The system of claim 17, wherein the applied test pacing pulse that triggers the adjusting of the initial evoked response amplitude threshold has an energy level above the predetermined maximum desirable pulse energy of the levels of pulse energy.

19. The system of claim 16, wherein the lower value for the evoked response amplitude threshold is a minimum value measurable above zero.

20. The system of claim 19, wherein the control circuit is further configured to generate a warning signal in response to adjusting of the initial evoked response amplitude threshold to the lower value.

* * * * *